US009724019B2

(12) United States Patent
Arvind et al.

(10) Patent No.: US 9,724,019 B2
(45) Date of Patent: Aug. 8, 2017

(54) METHOD, APPARATUS, COMPUTER PROGRAM AND SYSTEM FOR MEASURING OSCILLATORY MOTION

(75) Inventors: Damal Arvind, Edinburgh (GB); Andrew Bates, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 798 days.

(21) Appl. No.: 13/702,014

(22) PCT Filed: May 16, 2011

(86) PCT No.: PCT/GB2011/050934
§ 371 (c)(1),
(2), (4) Date: Feb. 19, 2013

(87) PCT Pub. No.: WO2011/151634
PCT Pub. Date: Dec. 8, 2011

(65) Prior Publication Data
US 2013/0172769 A1    Jul. 4, 2013

(30) Foreign Application Priority Data

Jun. 4, 2010  (GB) .................................. 1009379.7

(51) Int. Cl.
*A61B 5/113*    (2006.01)
*A61B 5/08*    (2006.01)
(Continued)

(52) U.S. Cl.
CPC ............ *A61B 5/113* (2013.01); *A61B 5/0004* (2013.01); *A61B 5/0816* (2013.01);
(Continued)

(58) Field of Classification Search
None
See application file for complete search history.

(56) References Cited

U.S. PATENT DOCUMENTS 2,676,206 A     4/1954  Bennett et al.
5,687,714 A *  11/1997  Kolobow .......... A61M 16/0463
                                                              128/201.11
(Continued)

FOREIGN PATENT DOCUMENTS

EP          1271099          1/2003
WO     WO/03/005893          1/2003
(Continued)

OTHER PUBLICATIONS

Translated Chinese Office Action for Chinese Patent Application No. 201180027571.9, mailed May 12, 2014, a counterpart foreign application of U.S. Appl. No. 13/702,014, 24 pages.
(Continued)

*Primary Examiner* — Jacqueline Cheng
*Assistant Examiner* — Jairo Portillo
(74) *Attorney, Agent, or Firm* — Lee & Hayes, PLLC

(57) ABSTRACT

A method, apparatus, computer program, system and device for measuring oscillatory motion comprising: receiving a plurality of signals related to a plurality of measurements of a direction of a vector parameter $(a_{t-1}, a_t)$; determining a predominant measured direction of the vector parameter $(\bar{a}_t)$ based on the plurality of measurements of the direction of the vector parameter; determining an angle of rotation $(\phi_t)$ between: a measured direction of the vector parameter $(a_t)$ of one of the plurality of measurements of the direction of the vector parameter, and the predominant measured direction of the vector parameter $(\bar{a}_t)$.

17 Claims, 9 Drawing Sheets

(51) Int. Cl.
*A61B 5/11* (2006.01)
*G01H 1/00* (2006.01)
*A61B 5/00* (2006.01)

(52) U.S. Cl.
CPC .......... *A61B 5/1116* (2013.01); *A61B 5/1121* (2013.01); *A61B 5/6801* (2013.01); *A61B 5/72* (2013.01); *G01H 1/00* (2013.01); *A61B 2562/0219* (2013.01); *A61B 2562/0223* (2013.01)

(56) References Cited

U.S. PATENT DOCUMENTS

| | | | |
|---|---|---|---|
| 6,997,882 B1 * | 2/2006 | Parker et al. | 600/534 |
| 8,032,324 B1 * | 10/2011 | Bryant et al. | 702/141 |
| 2005/0027216 A1 | 2/2005 | Guillemaud et al. | |
| 2006/0069322 A1 * | 3/2006 | Zhang et al. | 600/512 |
| 2006/0217598 A1 * | 9/2006 | Miyajima et al. | 600/300 |
| 2008/0015457 A1 | 1/2008 | Silva | |
| 2008/0132334 A1 * | 6/2008 | Nonaka et al. | 463/37 |
| 2009/0062628 A1 | 3/2009 | Yamamoto et al. | |
| 2009/0292178 A1 | 11/2009 | Ellis et al. | |
| 2010/0305480 A1 * | 12/2010 | Fu et al. | 600/595 |
| 2010/0324437 A1 * | 12/2010 | Freeman | A61B 5/085 600/529 |

FOREIGN PATENT DOCUMENTS

| | | |
|---|---|---|
| WO | WO2006/123691 A1 | 11/2006 |
| WO | W02009/138896 | 11/2009 |

OTHER PUBLICATIONS

Khoo, et al., "Wireless On-Body Network Breathing Rate and Depth Measurement During Activity", 30th Annual International IEEE EMBS Conference, Aug. 2008, pp. 1283-1287.

Konno, et al., "Measurement of the Separate Volume Changes of Rib Cage and Abdomen During Breathing", Journal of Applied Physiology, vol. 22, No. 3, Mar. 1967, 17 pages.

Smith, et al., "Three Degree of Freedom Description of Movement of the Human Chest Wall", Journal of Applied Physiology, vol. 60, No. 3, Mar. 1986, 8 pages.

* cited by examiner

METHOD, APPARATUS, COMPUTER PROGRAM AND SYSTEM FOR MEASURING OSCILLATORY MOTION

CROSS REFERENCE TO RELATED APPLICATIONS

This application is a 35 U.S.C. 371 National Stage Application of International Application No. PCT/GB2011/050934, filed May 16, 2011, which claims priority to GB1009379.7, filed on Jun. 4, 2010, the entire contents of which are incorporated herein by reference.

FIELD OF THE INVENTION

Embodiments of the present invention relate to a method, apparatus, computer program and system for measuring oscillatory motion. In particular, they relate to a method, apparatus, computer program and system for measuring oscillatory motion related to respiration.

BACKGROUND TO THE INVENTION

The measurement of patient's respiration is useful in the monitoring and diagnosis of a wide range of respiratory disorders, as well as being a useful broader metric of a patient's condition. Measurements of interest may include respiratory rate (breaths per minute, BPM), flow, tidal volume, breathing pattern as well as changes in these over time.

Devices for monitoring breathing typically fall into 3 main categories:
i) those that observe the movement or tissue composition of the abdomen and/or chest,
ii) those that measure the flow of air, and
iii) those that measure concentrations of different gases in the blood or expired air Devices of type i) may involve the measuring of: transthoracic and abdominal impedance, a circumference through strain, pressure or fiber-optic gauges embedded in belts and straps, electrical activity of the muscles involved in breathing (electromyography). Several of these devices require the use of obtrusive constrictive belts placed around the chest and abdomen which may not be conducive to continuous or long term monitoring, particularly for patients with certain conditions. Other devices require expensive and complex infrastructure around the patient and/or require a stationary patient to take measurements since patient movement disrupts the measurements, which effectively precludes the ability for home monitoring.

Where a patient requires Oxygen therapy, this can interfere with certain devices of type ii) which measure nasal gas flow. Also, mouth breathing cannot be measured with devices such as a cannula. Furthermore, a device measuring total breathing gas flow, such as a face mask, may be obtrusive and uncomfortable for patients, thus limiting the ability for continuous or long term monitoring of measurements.

Devices of type iii) tend not to give a reliable indication of changes in tidal volume and may react slowly to disruptions in breathing. Such devices are often obtrusive and not conducive to continuous or long term or remote home monitoring.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

BRIEF DESCRIPTION OF VARIOUS EMBODIMENTS OF THE INVENTION

According to various, but not necessarily all, embodiments of the invention there is provided a method for measuring oscillatory motion comprising: receiving a plurality of signals related to a plurality of measurements of a direction of a vector parameter $(a_{t-1}, a_t)$; determining a predominant measured direction of the vector parameter $(\bar{a}_t)$ based on the plurality of measurements of the direction of the vector parameter; determining an angle of rotation $(\phi_t)$ between: a measured direction of the vector parameter $(a_t)$ of one of the plurality of measurements of the direction of the vector parameter, and the predominant measured direction of the vector parameter $(\bar{a}_t)$.

The vector parameter may be a three dimensional vector which relates to for example: a gravitational field, a magnetic field or an angular orientation measured by a sensor. The sensor provides signals indicative of a measurement of a direction of the vector parameter relative to the sensor's measurement frame of reference, for example: a direction of the earth's gravitational field (e.g. a direction downwards in the sensor's frame), a direction of the earth's magnetic field (e.g. a direction north in the sensor's frame) or an orientation of the sensor. Movement of the sensor, in particular rotational movement, causes the direction of vector parameter in the sensor's frame to change.

In some embodiments, the sensor is coupled to a body part, for example a thorax, torso, chest or ribcage region of a patient at rest whose respiration is to be monitored, i.e. the sensor is located and attached to a part of the body which undergoes oscillatory movement during respiration. During the respiration process, the thorax region undergoes oscillatory movement as the lungs expand and contract. This movement causes corresponding movement of the attached sensor which alters the measured direction of the vector parameter within the frame of the sensor, i.e. it too undergoes an oscillatory movement. Readings of the direction of the vector parameter are taken. A predominant or average direction of the measured direction of the vector parameter is determined from a plurality of measurements over a period of time. The calculated predominant direction provides a base of reference for use in determining an angle of rotation due to the movement. The angle of rotation is defined as the angle between a measured direction of the vector parameter and the predominant measured direction of the vector parameter.

Embodiments provide a new metric for measuring oscillatory movement which is directly related to a physical parameter, e.g. rotation of an object during oscillatory motion or rotation of a patient's chest wall during respiration. Advantageously, the metric is an angular value that is determined relative to a reference direction which is determined from the measurements themselves, as opposed to being an absolute angular value that is relative to some constant or fixed reference direction. Thus, were there to be a large scale movement, unrelated to the oscillatory movement, which shifts the reference direction within the sensor's frame, the reference direction can be re-determined.

Various but not necessarily all embodiments provide the advantage that a measurement value, the angle of rotation, is determined which directly relates to a physical measurement, namely the angular motion induced by an oscillatory motion. In the case of respiration measurement, e.g. measurements related to the act of breathing where measurements are taken of the torso, the angular value directly relates to angular movement of torso during respiration with respect to a determined reference direction which corresponds to an average/central direction in the oscillating motion. The angle of rotation is determined relative to the determined reference direction, and so is independent of the initial orientation of a patient and the sensor device which captures the measurements. Thus, precise and careful initial placement of the sensor onto a patient is not required.

Various but not necessarily all embodiments may improve the ability to provide continuous unobtrusive respiratory monitoring. Embodiments may provide the ability to adapt and adjust to patient re-orientation or large scale movement by re-setting the reference direction against which the angle of rotation is determined. Various embodiments do not require restraining apparatus or complex and bulky infrastructure nor the involvement or medical practitioners and thus can enable low cost and long term remote respiratory monitoring.

According to various, but not necessarily all, embodiments of the invention there is provided a method which further includes:
determining a predominant axis of rotation about which the direction of the measured vector parameter rotates and further determining the angle of rotation based on rotation about the predominant axis of rotation.

The resultant determined angle relates to an angle of rotation about the predominant axis of rotation between: the measured direction of the vector parameter and the predominant measured direction of the vector parameter. In effect, such embodiments provide for the determination of an angle which is a projection of the angle of rotation onto a plane perpendicular to the predominant axis of rotation.

By only considering one dimensional angular motion projected onto a surface such as a plane perpendicular to the predominant axis of rotation, this provides the advantage that the quality and accuracy of the resultant determined angle is improved since any extraneous measurement signals or noise, e.g. due to movements/rotations in other planes which are not due to respiratory related movement are ignored. In various but not all embodiments, the determined angle of rotation is only concerned with rotations about the predominant axis of rotation. Thus, such embodiments provide an enhanced metric for measuring respiration.

According to various, but not necessarily all, embodiments of the invention there is provided a method which further includes:
determining a rotation angle ($\theta$) between: a measured direction of the vector parameter ($a_{t-1}$) and a sequential measured direction of the vector parameter ($a_t$).

If the rotation angle ($\theta$) is found to be greater than or equal to a threshold value, this may be indicative of substantial movement which would affect the direction of the predominant direction of the vector parameter as well as the predominant axis of rotation thereby disrupting the determined angle of rotation. Such substantial or "macro" movement of the patient relates to movement which is not related to the relative "micro" movement of the oscillating movement to be measured. Upon detection of exceeding the threshold, the predominant direction of the vector parameter and predominant axis of rotation are re-determined. Such features provide the ability to distinguish valid measurement signals from invalid measurement signals and enable the classification of periods between the threshold being exceeded where the patient is static and measurements can be taken which are not overwhelmed by substantial movement. Advantageously, this enables embodiments to adopt and adjust to substantial movements which would otherwise cause a shift in the reference direction and lead to inaccurate measurements.

According to various, but not necessarily all, embodiments of the invention there is provided a method which further includes:
determining an angular velocity ($\omega$) based on angle of rotation ($\phi$).

Advantageously, the inventors have found that the value of angular velocity closely corresponds to respiratory flow rate. Thus, advantageously, embodiments can be used to provide a metric that relates to respiratory flow rate.

According to various, but not necessarily all, embodiments of the invention there is provided an apparatus for measuring oscillatory motion comprising: a memory storing computer program instructions; a processor configured to execute the computer program instructions to cause the apparatus at least to perform the above methods.

According to various, but not necessarily all, embodiments of the invention there is provided a computer program that, when run on a computer, performs the above methods.

According to various, but not necessarily all, embodiments of the invention there is provided an apparatus for measuring oscillatory motion comprising: an input interface arranged to receive a plurality of signals related to a plurality of measurements of a direction of a vector parameter; a controller arranged to determine a predominant direction of the vector parameter based on the plurality of measurements of the direction of the vector parameter; and the controller further arranged to determine an angle of rotation between: a measured direction of the vector parameter of one of the plurality of measurements of the direction of the vector parameter and the predominant measured direction of the vector parameter.

According to various, but not necessarily all, embodiments of the invention there is provided a system or device for measuring oscillatory motion comprising: means for measuring a direction of a vector parameter; means for generating a signal related to the direction of a vector parameter; means for transmitting the signal; and the above apparatus.

BRIEF DESCRIPTION OF THE DRAWINGS

For a better understanding of various examples of embodiments of the present invention reference will now be made by way of example only to the accompanying drawings in which.

DETAILED DESCRIPTION OF VARIOUS EMBODIMENTS OF THE INVENTION

Figure 1:
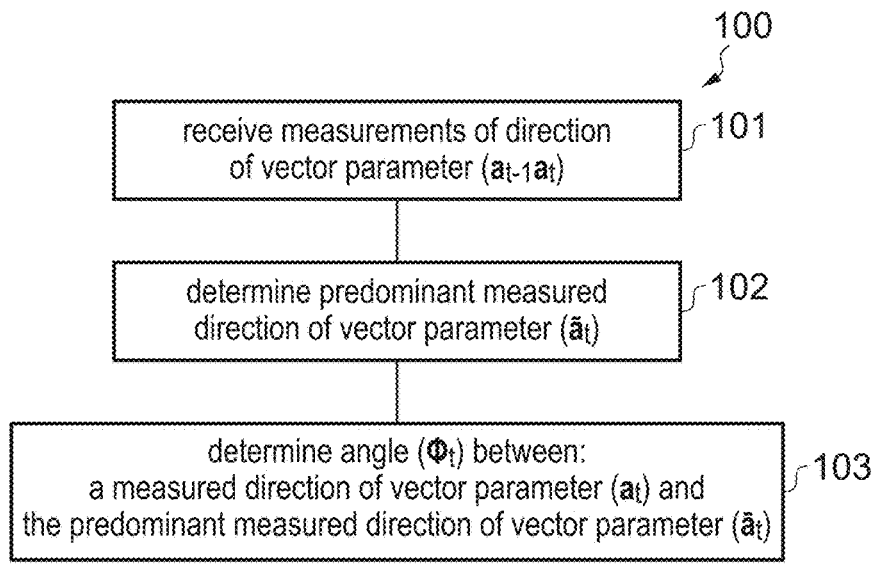
FIG. 1 schematically illustrates a flow diagram of a method for measuring oscillatory motion.

FIG. 1 schematically illustrates a flow diagram of a method 100 for measuring oscillatory motion. In block 101, a plurality of measurements of a direction of a vector parameter at given points in time ($a_{t-1}$, $a_t$) are received.

The measurements of the vector parameter are captured by a sensor which is fixedly attached or physically coupled to the object whose oscillatory movement is to be measured, such that the sensor is kept in a stable and steady position with respect to the object so that movement of the object causes corresponding movement of the sensor. The measurements are captured at a predetermined frequency. Preferably, the frequency is set such that a plurality of measurements is captured over the duration of a single cycle of the oscillatory motion.

In some embodiments, the sensor is fixedly attached directly or indirectly to a body part, for example a thorax, torso, chest, abdomen or ribcage region of a patient whose respiration is to be monitored, or a garment of the patient. The sensor is located and attached to a part of the body which undergoes oscillatory movement during respiration. The sensor may be directly or indirectly physically coupled to the body part by any suitable means such as, for example, via fixing/attaching means or adhesion. Preferably, the sensor device is affixed to the lower boundary of a patient's false ribs, on the mid clavicular line to maximize the amplitude of the measured oscillatory motion. Also, simultaneous placement of another sensor device on the thoracic cage and the abdomen would allow the capture of different stages and characteristics of breathing.

The vector parameter may be a three dimensional vector which relates to: a gravitational field, a magnetic field or an angular orientation measured by a sensor. The sensor provides signals indicative of a measurement of a direction of the vector parameter in the sensor's measurement frame of reference, for example: a direction of the earth's gravitational field (e.g. a direction downwards in the sensor's frame), a direction of the earth's magnetic field (e.g. a direction north in the sensor's frame) or an orientation of the sensor. Movement of the sensor, in particular oscillatory rotational movement, causes the direction of vector parameter in the sensor's frame to change.

Where the sensor is an accelerometer, due to the minor linear accelerations involved in the motions due to breathing, the measured acceleration vector parameter will be close to the acceleration due to gravity g whilst the patient is at rest and breathing. As the sensor rotates, the gravity vector would rotate in the co-ordinate frame of the sensor. The plurality of measurements enables the gravity vector's direction with respect to the sensor's frame of reference to be tracked during the oscillatory movement induced by breathing.

In block 102, a predominant direction of the vector parameter ($\bar{a}_t$) over a pre-determined period of time (W) is determined. This corresponds to an average direction of the vector parameter in the sensor's frame over the pre-determined period of time. Preferably, the time period over which measurements are taken is greater than or equal to the duration of one cycle of the oscillatory motion, e.g. the duration of a breath or a respiration cycle. This enables measurements to be captured over at least one entire cycle of oscillatory motion.

The predominant direction of the vector parameter $\bar{a}_t$ can be calculated as:

$$\bar{a}_t = \text{normalise}\left(\sum_{i=-\frac{W}{2}}^{\frac{W}{2}} a_{t+i}\right)$$

In block 103, an angle of rotation ($\phi_t$) is determined. This angle is defined as the angle between:

one of the measured directions of the vector parameter ($a_t$), and the predominant measured direction of the vector parameter ($\bar{a}_t$).

The angle of rotation $\phi_t$ can be calculated as:

$$\phi_t = \cos^{-1}(a_t \cdot \bar{a}_t)$$

An angular rotation rate or angular velocity $\omega_t$ of the angle of rotation $\phi_t$ can be determined. This can be calculated by taking the derivative $\omega_t$ of $\phi_t$ i.e.

$$\omega_t = \frac{d\phi}{dt}$$

Where the angular velocities are related to respiration, other respiration parameters can be determined from the angular velocities by applying various different algorithms to determine: breathing rates, breathing variability and changes in chest expansion.

Figure 2:
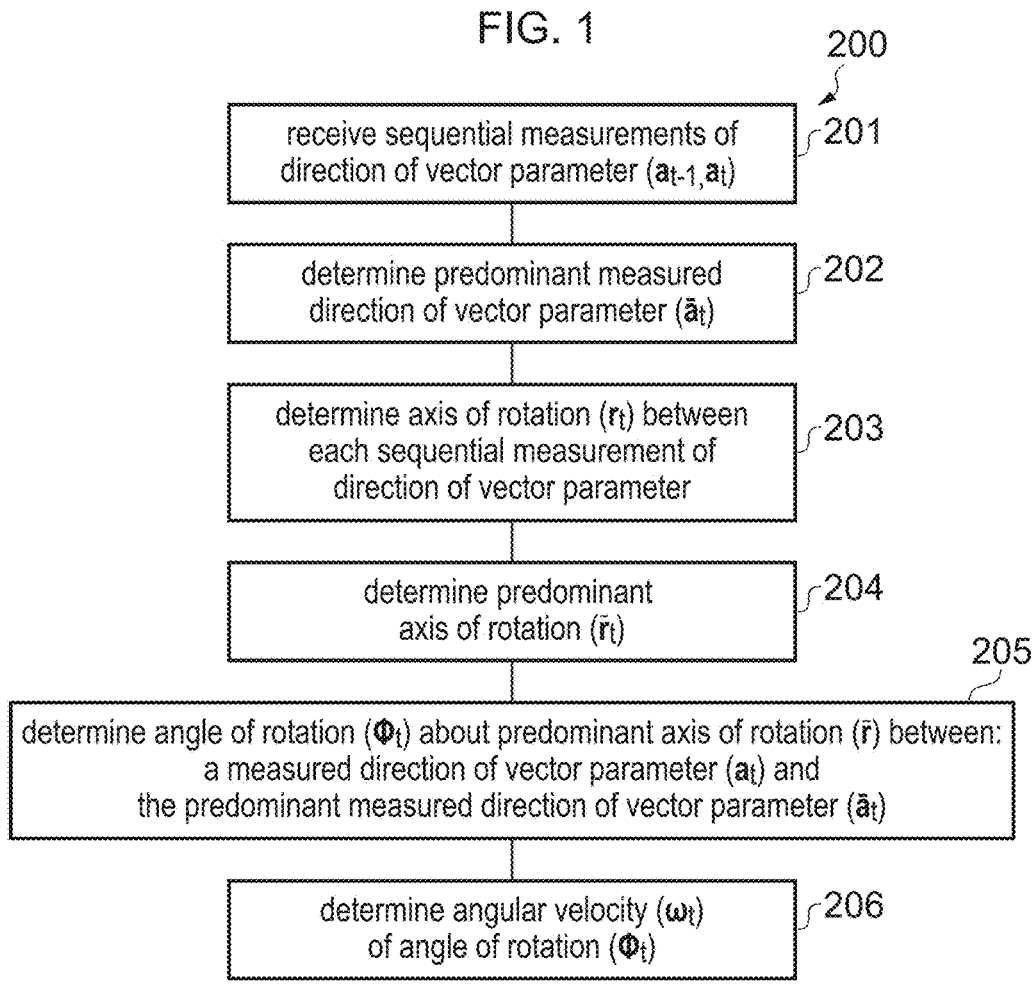
FIG. 2 schematically illustrates a flow diagram of another method for measuring oscillatory motion.

FIG. 2 schematically illustrates a flow diagram of another method 200 for measuring oscillatory motion which involves the determination of the axes of rotation of the vector parameter.

As the sensor rotates, the measured vector parameter (e.g. the measured gravity vector, magnetic vector or orientation vector) rotates in the co-ordinate frame of the sensor. However, the axis of this rotation may be arbitrarily orientated in the sensor frame, and may change due to differences in the way the patient breathes at different times. The orientation of the axis can also change following a large scale movement, i.e. unrelated to the oscillatory movement, such as a change in the overall orientation of the patient. In order to reduce the affect of noise in measured signals, it is advantageous only to consider rotations about the axis of rotation. Thus, it is desirable to determine the axis of rotation and track it as it changes.

In block 201, a plurality of measurements of directions of a vector parameter ($a_{t-1}$, $a_t$) are received. The measurements comprise pairs of sequentially measured measurements of the vector parameter.

Similarly to block 102, in block 202 a predominant direction of the vector parameter ($\bar{a}_t$) is determined.

In block 203, an axis of rotation ($r_t$) between each pair of sequential measurements ($a_{t-1}$, $a_t$) is determined. The axis of rotation it can be calculated as:

$$r_t = a_t \times a_{t-1}$$

For an oscillatory rotation, $r_t$ will invert when the direction of rotation reverses. Accordingly, the axis direction is normalized ($r_t'$) so as to be within a chosen hemisphere by comparison to a reference axis ($r_{ref}$). The normalized axis of rotation direction $r_t'$ can be calculated as:

$$r_t' = \begin{cases} r_t, & r_t \cdot r_{ref} \geq 0 \\ -r_t, & r_t \cdot r_{ref} < 0 \end{cases}$$

The value of $r_{ref}$ can be selected manually, or chosen automatically based on initial observations, such as by performing principal components analysis on the values of $r_t$.

In block 204, a predominant axis of rotation ($\bar{r}_t$) is determined. This corresponds to an average axis of the axes of rotation determined in block 203. Again, this is determined over a pre-determined period of time (W).

The predominant axis of rotation $\bar{r}_t$ could be calculated by taking an average of all the normalized axes of rotation $r_t'$ over a pre-determined period of time (W), i.e.:

$$\bar{r}_t = \left( \sum_{i=-\frac{W}{2}}^{\frac{W}{2}} r'_{t+i} \right)$$

Alternatively, in order to reduce the effect of noise on the determination of the mean $\bar{r}_t$, each normalized axis of rotation direction $r_t'$ could be suitably weighted, for example by an angle change $\phi_t$ associated with each pair of sequentially measured measurements of the vector parameter ($a_{t-1}$, $a_t$). Also, to give a greater weight to estimates closer in time to t, a Hamming window function H(n) can be used, i.e.:

$$\bar{r}_t = \text{normalise} \left( \sum_{i=-\frac{W}{2}}^{\frac{W}{2}} H(i) \theta_{t+i} r'_{t+i} \right)$$

where:

$$\theta_t = \cos^{-1}(a_t \cdot a_{t-1})$$

In block 205, an angle of rotation $\phi_t$ is determined which is defined as an angle of rotation about the predominant axis of rotation ($\bar{r}_t$) between:
  a measured direction of the vector parameter ($a_t$) and
  the predominant direction of the vector parameter ($\bar{a}_t$).

The angle of rotation $\phi_t$ can be calculated as:

$$\phi_t = \sin^{-1}((\bar{a}_t \times \bar{r}_t) \cdot a_t)$$

One can consider block 205 as further determining the angle of rotation which was determined in FIG. 1's block 103 by a projection of block 103's angle of rotation onto a surface. In block 205, the surface corresponds to a plane, defined as a plane perpendicular to the predominant axis of rotation $\bar{r}_t$. However, it would be possible for other projection surfaces to be considered, such as for example, a projection of block 103's angle of rotation onto a surface of an ellipsoid. To effect this, the initial measurements of directions of a vector parameter ($a_{t-1}$, $a_t$) could be appropriately modified by application of a suitable function f(a).

In block 206, the angular rotation rate or angular velocity $\omega_t$ of the angle of rotation $\phi_t$ is determined. This can be calculated by taking the derivative $\phi_t$ of, i.e.

$$\omega_t = \frac{d\phi}{dt}$$

Figure 3:
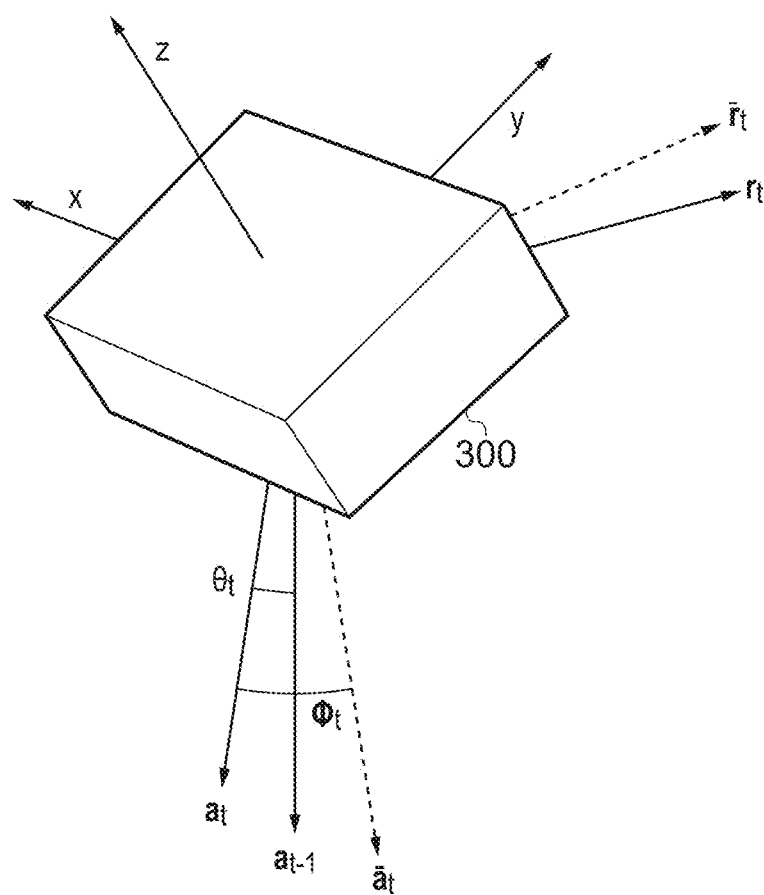
FIG. 3 schematically illustrates an example of a sensor for measuring oscillatory motion.

FIG. 3 schematically illustrates an example of a sensor device 300 for measuring oscillatory motion. In particular, the figure provides a representation of the various axes and vectors used above.

The sensor device comprises sensors that can give an indication of movement of the device. For example:
  an accelerometer that can detect changes in the measured direction of the earth's gravitational field (such as a Freescale® MMA7260QT tri-axial accelerometer)
  a magnetometer that can detect changes in the measured direction of the earth's magnetic field (such as a Honeywell® HMC1052 twin axis magnetometer), or
  a gyroscope that can detect changes in the sensor's orientation (such as Analog Devices® ADXRS300 rate gyroscopes).

The sensor device is configured to provide measurements that enable a vector quantity, such as three dimensional representation of the orientation of the sensor device, to be determined.

The sensor device's co-ordinate plane is shown as three orthogonal axes: x, y and z. The sensor device comprises a tri-axial sensor able to measure the vector parameter in each of three orthogonal axes or dimensions. The use of a tri-axial device allows inclination changes to be measured regardless of orientation. If the sensor device is placed on an object which undergoes oscillatory rotation over time, then the measured directions of a vector parameter within the sensor device's frame of measurement ($a_{t-1}$, $a_t$) would alter as indicated. The predominant direction of the vector parameter $\bar{a}_t$ relates to an average direction of the measured directions of the vector parameter over time.

The axis of rotation $r_t$ relates to an axis about which a first measured direction $a_{t-1}$ of the vector parameter rotates with respect to a second measured direction of the vector parameter $a_t$. The angle through which the direction of the vector rotates is the angle change $\theta_t$. The axis of rotation is perpendicular to each of the first and second measured vector parameters.

The predominant axis of rotation $\bar{r}_t$ relates to an average of the axes of rotation. The angle of rotation ($\phi_t$) relates to the angle between: one of the measured directions of the vector parameter ($a_t$), and the predominant measured direction of the vector parameter ($\bar{a}_t$). In the method of FIG. 2, the angle is additionally defined as being based on rotation about the predominant axis of rotation $\bar{r}_t$.

In various but not necessarily all embodiments, accelerometers are employed to measure a vector parameter. It may seem counterintuitive to employ an accelerometer to measure an angle and angular rate, when gyroscopic microelectromechanical systems (MEMS) exist which can do this directly. However, advantageously, accelerometer-based sensors have a lower power consumption than gyroscopic based sensors. For example, current tri-axial MEMS accelerometers can have active current consumptions of as little as 40 μA, permitting very long term monitoring with small battery-powered devices, whereas, integrated tri-axial MEMS gyroscopes have a current consumptions of the order of 10 mA.

When a patient undergoes large scale movement, e.g. which results in a change of body position, the accelerometer based measurement method during such a period of motion is likely infeasible since the magnitude of the movement-induced signals due to patient movement, i.e. movement unrelated to the oscillatory movement under investigation, vastly exceeds the oscillatory movement due to breathing. Thus, it is desirable to detect such movements so that measurements captured around the time of such movement are ignored as they would not reliably relate just to the oscillatory motion under investigation. Furthermore, following a patient re-orientation, the predominant direction of the vector and the predominant axis of rotation are likely to have altered and thus would need to be re-calculated.

Figure 4:
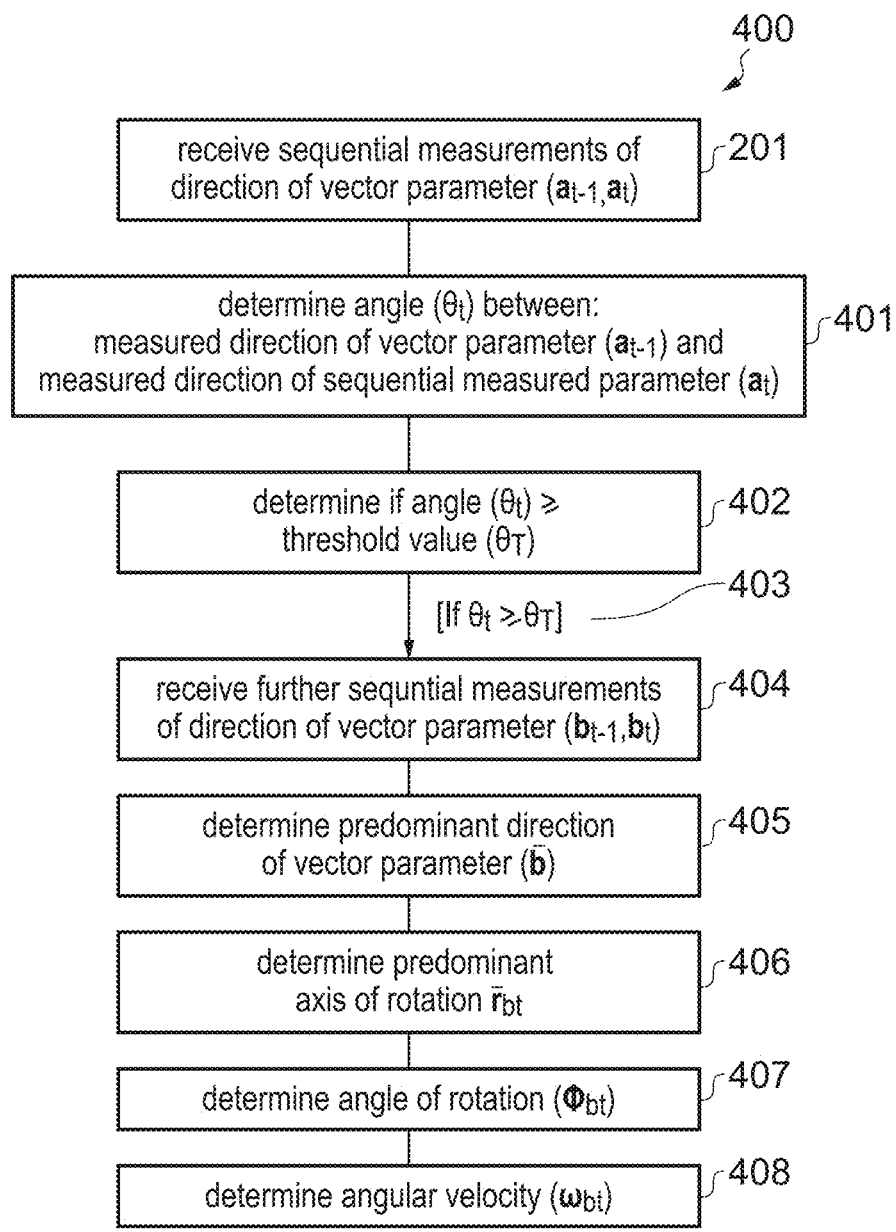
FIG. 4 schematically illustrates a flow diagram of another method for measuring oscillatory motion.

FIG. 4 schematically illustrates a flow diagram of another method 400 for measuring oscillatory motion which addresses such issues and provides a method to distinguish periods when the patient is at rest and measurements can reliably be taken and periods when the patient is moving/re-orientating, during which measurements may be disregarded.

The method 400 follows on from the previously described methods of FIG. 2 including block 201 in which a plurality of measurements of directions of a vector parameter $(a_{t-1}, a_t)$ are received.

In block 401, the method 400 includes the determination of a change in the pair of sequentially measured measurements of the vector parameter $(a_{t-1}, a_t)$. The change could be a change in magnitude or a change in direction of the measured vector parameter between sequential measurements. Block 401 shows the determination of an angle change $\theta_t$ associated with each pair of sequentially measured measurements of the vector parameter $(a_{t-1}, a_t)$, e.g.

$$\theta_t = \cos^{-1}(a_t \cdot a_{t-1}).$$

In block 402, the change in the measured vector parameter is compared to a threshold value, e.g. $\theta_T$. The threshold value is set at a pre-determined value that exceeds the amount of change one would expect to be feasible for the oscillatory motion under investigation. For example, with regards to measuring respiration, a sudden increase in the measured acceleration between two consecutive readings would likely indicate macro scale movement of the patient, i.e. the sensor would have picked up movement of the patient which is not related to breathing. Were the sensor to use measurements of movements unrelated to breathing, this would lead to erroneous measurements. Thus, the features of FIG. 4 provide a method to detect such large scale movements unrelated to the oscillatory movements to be measured. Measurements captured which relate to such large scale movements could then be disregarded. Furthermore, following such movement, it is likely the orientation of the sensor may have substantially changed. This would alter the predominant measured direction of the vector parameter $(\bar{a}_t)$ in the sensor's frame of reference. Also, it would alter the predominant axis of rotation $(\bar{r}_t)$ in the sensor's frame of reference. Thus, these quantities would need to be re-determined.

If the determined change in the sequential measurements of the vector parameter exceed a threshold level, indicated by reference 403, then further measurements of a direction of the vector parameter are obtained $b_{t-1}$, $b_t$, (block 404) which are used to re-calculate the predominant measured direction of the vector parameter $\bar{b}$ (block 405) and a predominant axis of rotation $\bar{r}_{bt}$ (block 406) which are used to determine an angle of rotation $\phi_{at}$ (block 407) and an angular velocity $\omega_{bt}$ (block 408).

Thus, the determined values of the angle of rotation and the angular velocity are based on measurements captured during a time window during which no substantial movements took place, which would overwhelm the measurements of movement just related to breathing.

A range of measured measurements could be determined and used to provide an indication whether or not the measurements recorded are sub optimal. If the determined range of measurements is below a threshold level, this may indicate that the sensor is not adequately measuring the oscillatory movement. For example, the sensor might be inappropriately positioned or sub-optimally located on a body part that does not undergo the respiration related movement. Alternatively, the sensor may have become detached from the body part and thus, being no longer fixedly attached to it, does not follow its movements.

A degree of confidence of the angle of rotations and angular velocities can be determined based on a weighted sum of different measures of the quality of the measurements, for example: the amplitude of the measurements of the vector parameter, the noise level outside the frequencies relevant for the oscillatory motion, the degree of signal found to be outside of the plane of rotation and the angular consistency of the angular rotation rate.

Figure 5:
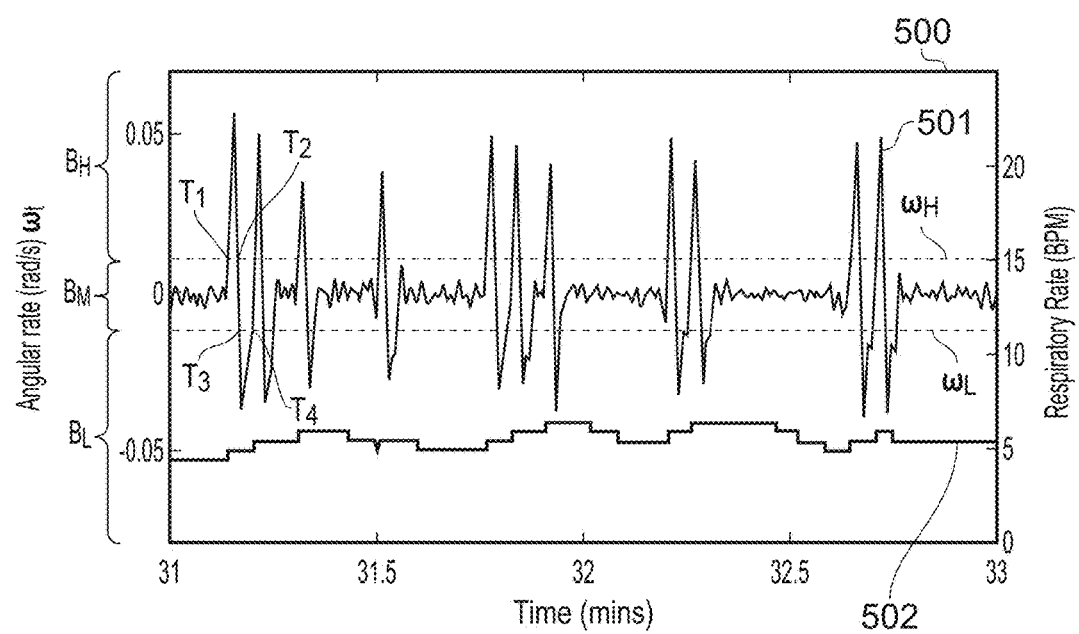
FIG. 5 illustrates a graph of angular rate and respiratory rate against time.

FIG. 5 illustrates a graph 500 of angular rate and respiratory rate 501 against time based upon measurements recorded with embodiments of the present invention. The graph also shows a respiratory rate 502 against time.

In order to provide a method of determining a respiratory rate, i.e. the number of breaths per minute, from measured angular velocities, a first band $(B_H)$ of range of angular velocity values is defined where the angular velocity value is greater that a first threshold value $(\omega_H)$. A second band $(B_L)$ of range of angular velocity values is also defined where the angular velocity value is less than a second threshold value $(\omega_L)$. A third band $(B_M)$ of range of angular velocity values are also defined where the angular velocity value is between the first and second threshold values $(\phi_H, \omega_L)$.

The values of sequential angular velocity measurements are monitored and a registration of a count corresponding to the completion of one cycle of the oscillatory motion, e.g. one breath, is recorded each time the values of angular velocity transition through four bands, e.g. $T_1$ from $B_M$ to $B_H$, $T_2$ from $B_H$ to $B_M$, $T_3$ from $B_M$ to $B_L$ and $T_4$ from $B_L$ to $B_M$. The respiration rate is then determined based on the number of counts within a measurement time period.

Prior approaches to determining a respiratory rate which involve spectral analysis of waveforms had difficulty detecting individual breaths where a patient's breathing pattern is irregular. Advantageously, the above state transition approach provides the ability to identify individual breaths, including breaths of irregular frequency. Also, it reduces problems of multiple breaths being registered from noisy signals as might occur with a single threshold method were repeated crossings through a single threshold would lead to erroneous results.

Figure 6:
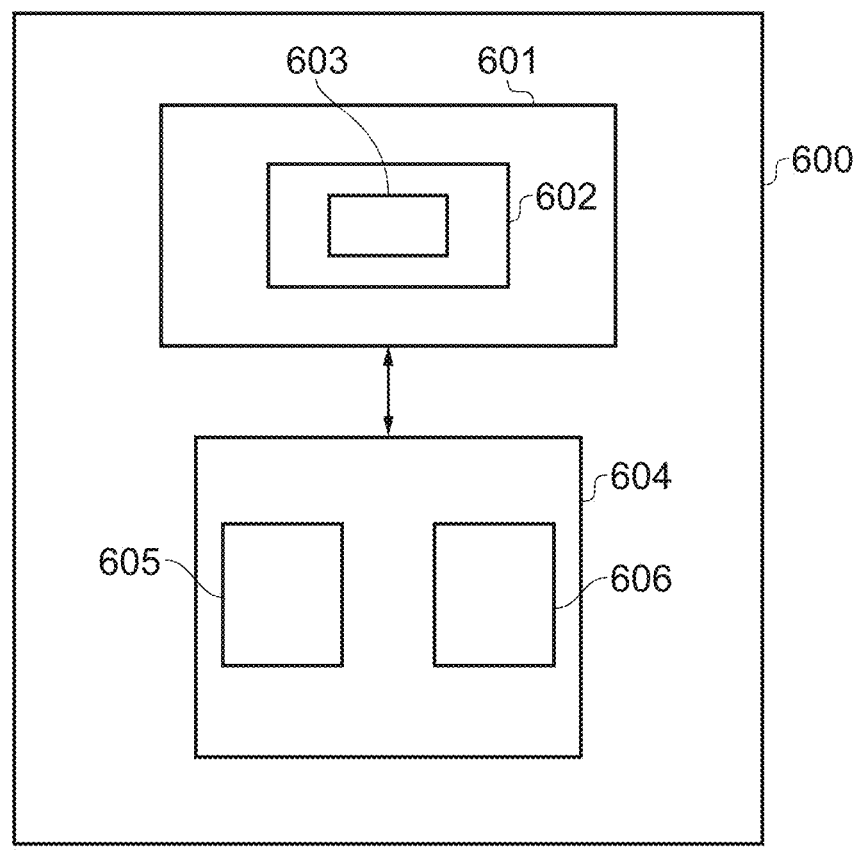
FIG. 6 schematically illustrates an example of an apparatus for measuring oscillatory motion.

FIG. 6 schematically illustrates an example of an apparatus 600 for measuring oscillatory motion.

The apparatus 600 comprises a controller such as a processor or digital signal processor 604; and a memory 601 including computer program 602 comprising program code 603. The memory 601 and the computer program code 603 are configured to, with the processor 604, cause the apparatus 600 at least to perform the methods described above with reference to FIGS. 1, 2 and 4.

The blocks illustrated in the FIGS. 1, 2 and 4 may represent steps in a method and/or sections of code in the computer program 602. The illustration of a particular order to the blocks does not necessarily imply that there is a required or preferred order for the blocks and the order and arrangement of the block may be varied. Furthermore, it may be possible for some steps to be omitted.

The processor 604 is configured to read from and write to the memory 601. The processor may also comprise an output interface 606 via which data and/or commands are output by the processor and an input interface 605 via which data and/or commands are input to the processor.

The memory 601 stores a computer program 602 comprising computer program instructions 602 that control the operation of the apparatus 600 when loaded into the processor 604. The processor 604, by reading the memory 601, is able to load and execute the computer program 602. The computer program instructions 603 provide the logic and routines that enable the apparatus to perform the methods illustrated in FIGS. 1, 2 and 4 and discussed above.

The computer program 602 may arrive at the apparatus 600 via any suitable delivery mechanism. The delivery mechanism may be, for example, a computer-readable storage medium, a computer program product, a memory device, a record medium such as a compact disc read-only memory or digital versatile disc, an article of manufacture that tangibly embodies the computer program 602. The delivery mechanism may be a signal configured to reliably transfer the computer program 602.

Implementation of the controller 604 can be in hardware alone (a circuit, a processor . . . ), have certain aspects in software including firmware alone or can be a combination of hardware and software (including firmware).

The controller 604 may be implemented using instructions 603 that enable hardware functionality, for example, by using executable computer program instructions in a general-purpose or special-purpose processor that may be stored on a computer readable storage medium (disk, memory etc) or carried by a signal carrier to be executed by such a processor.

Figure 7:
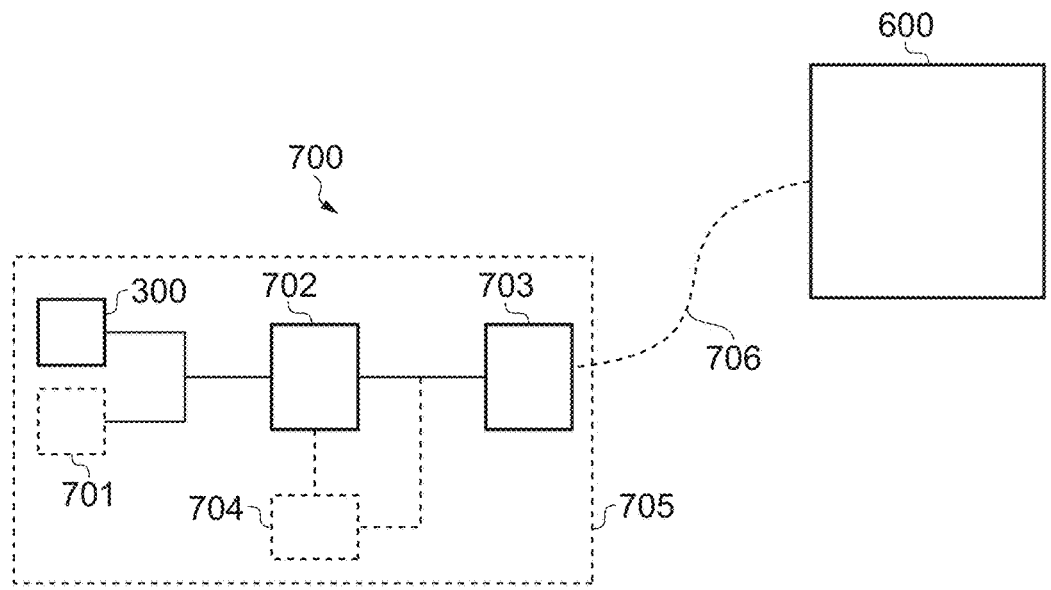
FIG. 7 schematically illustrates an example of a system for measuring oscillatory motion.

FIG. 7 schematically illustrates an example of a system 700 for measuring oscillatory motion. The system comprises means for measuring a direction of a vector parameter such as sensor devices 300 and 701 which are coupled to a means for generating a signal related to the direction of a vector parameter, such as a controller 702.

Preferably each sensor device is capable of measuring a vector parameter in 3 dimensions. Furthermore, where two or more sensor devices are employed, it is preferable that each measures a different vector parameter. For example, sensor device 300 is an accelerometer based sensor device for measuring gravitational fields and sensor device 701 is a magnetometer based sensor device for measuring magnetic fields. Where solely a single type of sensor device is employed, e.g. just accelerometer based, any component of rotations that lie in the vertical axis, i.e. aligned with direction of gravitational field, would not be detected or measured by the accelerometer. However, by additionally including another type of sensor such as a magnetometer or gyroscope, such rotations aligned with direction of gravitational field would be detectable and measureable. Similarly, where sensor is just magnetometer based, any component of rotations that lies along an axis aligned with direction of the earth's magnetic field would not be detected by the magnetometer. Additionally including an accelerometer or gyroscope would enable such rotations to be detected and measured.

The controller 702 is coupled to a means for transmitting the signal, such as a transmitter 703, to apparatus 600 as shown in FIG. 6. The transmission 706 could be effected via wired or preferably wireless communication to facilitate the remote capture and monitoring of measurements.

Optionally, storage 704 is provided to store the measurements so that measurements need not be constantly sent/transmitted as soon as they are measured. In some embodiments, the sensors, controller, transmitter and optional storage are all housed within housing 705. Preferably, the housing and internal components are dimensioned as small as possible so that the device is minimally obtrusive when attached to a patient. Such small housings may be attached to a patient with standard medical tape.

Figure 8:
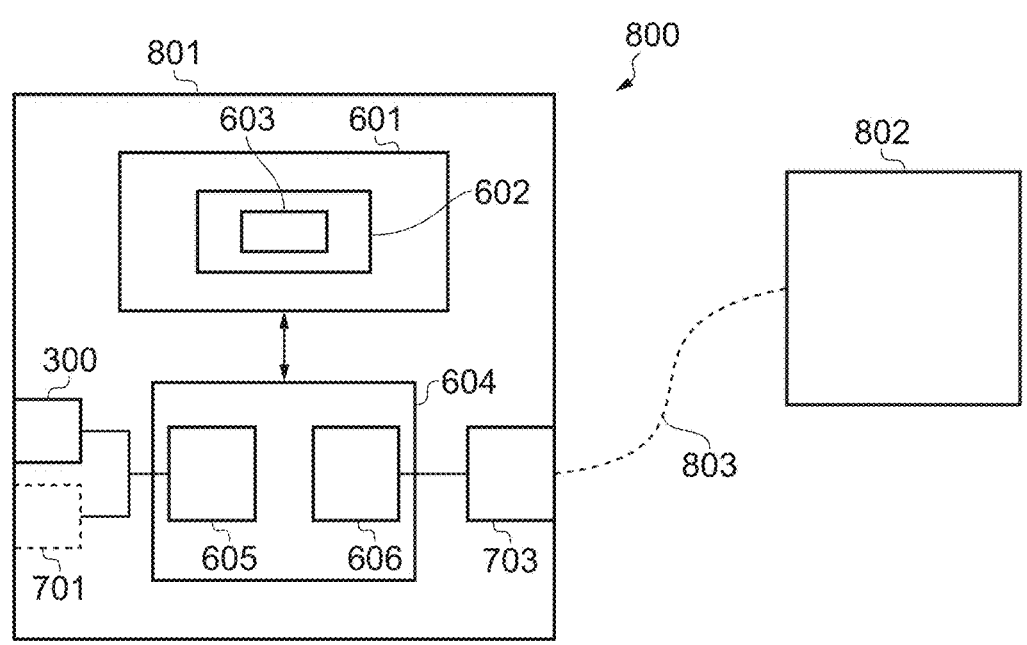
FIG. 8 schematically illustrates an example of a device for measuring oscillatory motion.

FIG. 8 schematically illustrates an example of a device 800 for measuring oscillatory motion. The device 800 effectively comprises the apparatus for processing the measurements signals, as discussed with regards to FIG. 6, and also sensor device 300 (and optionally 701) for measuring and generating the measurement signals all housed within housing 801.

The device 800 comprises a controller 604, memory 601, computer program 602 and program code 603. Sensor devices 300 and 701 capture measurements of different vector parameters which are received by the input interface 605 of the processor 605. The memory 601 and the computer program code 603 are configured to, with the processor 604, cause the device 801 at least to perform the methods described above with reference to FIGS. 1, 2 and 4. The determined angles of rotations $\phi_t$ and angular velocities $\omega_t$ are an output from interface 606 to transmitter 703 for wired or wireless transmission 803 to a base station, computing device or server 802. Preferably, the device 800 comprises its own on board power supply, such as batteries and the ability to re-charge the batteries (not shown).

Optionally, two or more devices are fixedly attached to a patient whose respiration is to be measured. At least one of the devices is fixedly attached to a body part that undergoes oscillatory motion due to respiration. At least one of the devices is fixedly attached to a body part that does not undergo oscillatory motion due to respiration. Measurements from the two or more devices can then be combined to remove measurement components not related to the oscillatory motion under investigation. This enables a more precise determination of components of the measurements that are solely related to respiration.

Figure 9:
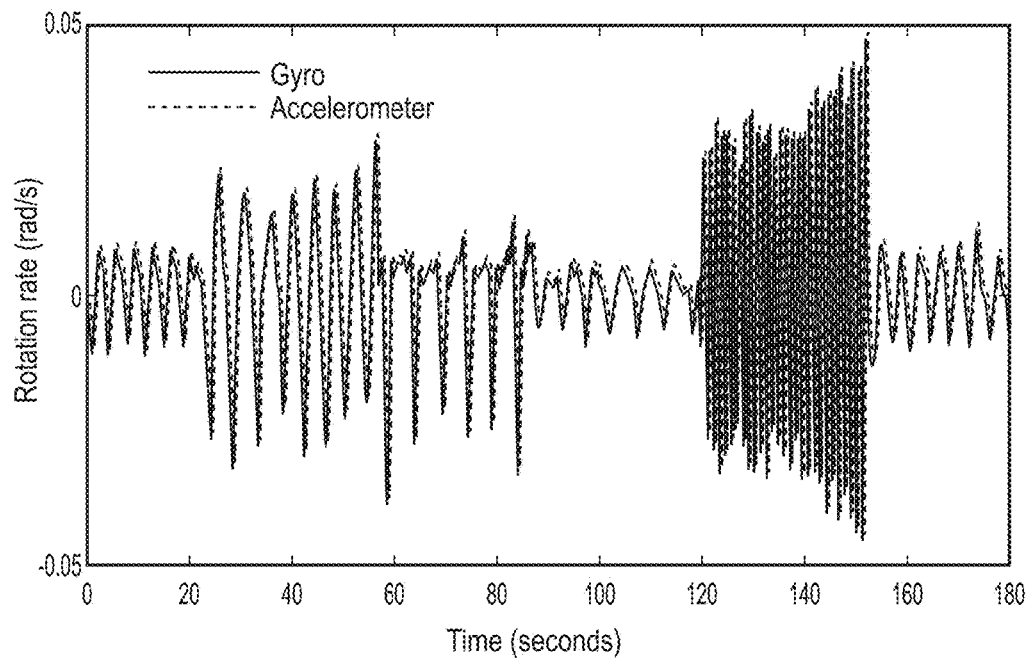
FIG. 9 illustrates a graph showing a comparison between a plot of angular rotation rates measured by an accelerometer based sensor according to an embodiment of the present invention and a plot of angular rotation rates measured by a gyroscopic sensor against time.

FIG. 9 illustrates a graph showing a comparison between angular rotation rates $\omega_t$ measured by each of an accelerometer based sensor according to an embodiment of the present invention and a gyroscopic sensor against time. As can be seen, the angular rates obtained from the accelerometer, having been appropriately scaled, provide a good match to angular rates obtained via a gyroscopic device. The graph shows a range of different breathing rates and depths which are visible from each plot.

Figure 10:
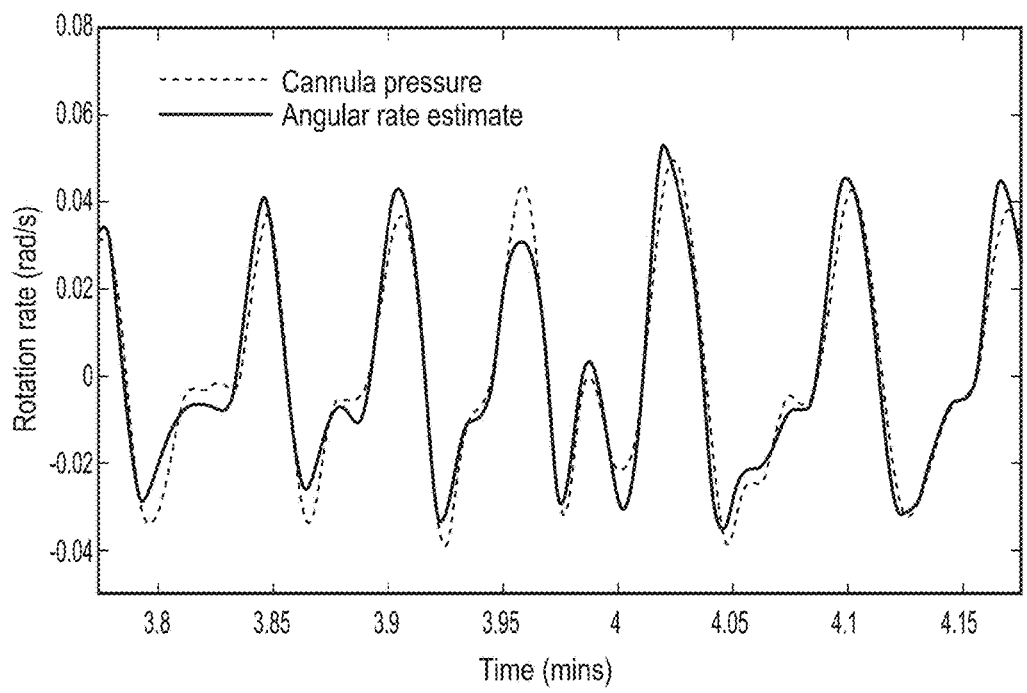
FIG. 10 illustrates a graph showing a comparison between rotation rates measured by an accelerometer based sensor according to an embodiment of the present invention and nasal cannula pressure against time.

FIG. 10 illustrates a graph showing a comparison between rotation rates $\omega_t$ measured by an accelerometer based sensor according to an embodiment of the present invention and nasal cannula pressure against time.

This graph illustrates the correspondence of angular rotation rates $\omega_t$ and a nasal cannula pressure measured by a pressure transducer (Respironics® PTAF2) connected to a nasal cannula. It is known that the cannula pressure is proportional to airflow rate for nasal breathing. Thus, the correlation shown in this graph also indicates the correlation between the angular rotation rates $\omega_t$ and flow rates. Furthermore, this is indicative of a correlation between the angular rotation rates $\omega_t$ and changes in the volume of the chest during breathing.

This correlation is important since the shape of a flow rate waveform provides significant additional information for diagnosis of respiratory problems that is not present in a simple measurement of the respiratory rate. Analysis of different inspiratory flow shapes suggests the shape of breaths can be a useful indicator of different respiratory conditions. It has also been shown that the shape can be used to identify obstructions.

An evaluation of an embodiment of the method, apparatus and system of the present invention was carried out in a 6.9 hour overnight capture of a post-operative patient. The key data from this evaluation is plotted in FIGS. 11A to E.

Figures 11A, 11B, 11C, 11D, 11E:
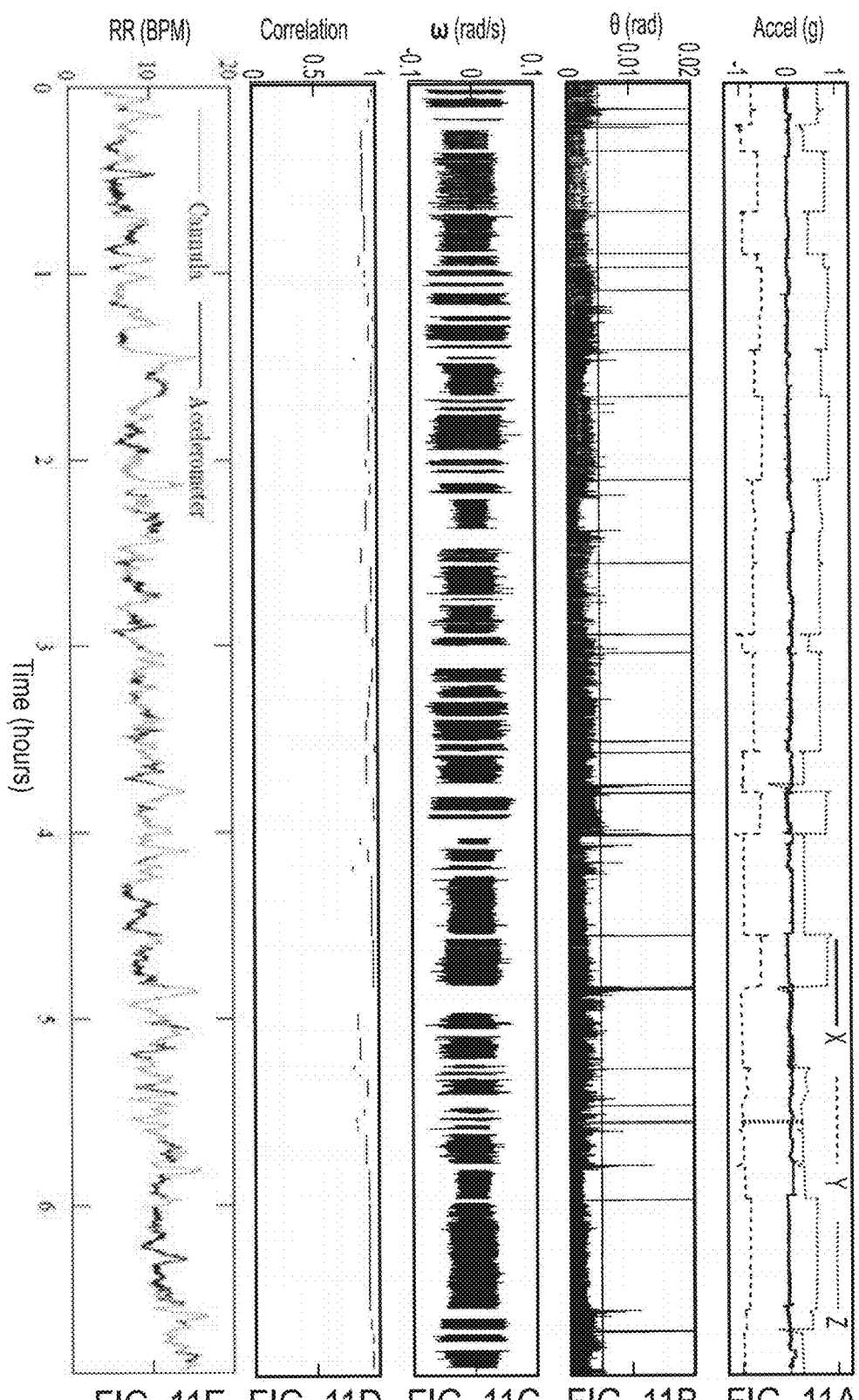
FIG. 11A illustrates a graph showing a tri-axial accelerometer signal against time.
FIG. 11B illustrates a graph showing the angle changes between consecutive acceleration vectors of FIG. 11A against time.
FIG. 11C illustrates a graph showing angular rates calculated from the accelerometer signal of FIG. 11A against time.
FIG. 11D illustrates a graph showing correlation coefficients between angular rates of FIG. 11C and cannula pressure against time.
FIG. 11E illustrates a graph showing respiratory rates calculated from the angular rates of FIG. 11C and respiratory rates calculated from cannula pressure derived data against time.

FIG. 11A illustrates a graph showing a tri-axial accelerometer signal against time in each of an: x axis (the middle plot) y axis (the lower plot) and z axis (the upper plot). Several large changes of patient orientation are visible as step changes in the acceleration on each axis.

FIG. 11B illustrates a graph showing the angle changes $\theta_t$ between consecutive acceleration vectors of FIG. 11A against time. There are clear spikes in this graph which correspond to major orientation changes, along with smaller peaks indicating lesser movements. The threshold value used for movement detection, $\theta_T$, is also shown. A threshold of 5 milliradians per $\frac{1}{16}$ s sample interval was used. The choice of threshold represents a tradeoff between accuracy and coverage. Lower thresholds increase the sensitivity to movement, discarding more of the dataset but achieving higher correlation to the cannula data for the periods retained.

FIG. 11C illustrates a graph showing angular rates calculated from the accelerometer signal of FIG. 11A against time. Individual breaths are not visible at this horizontal scale, but the plot illustrates the detected static periods over which the method algorithm was executed in contrast to the blank periods of no measurement caused by movement/reorientation of the patient, i.e. where angle changes $\theta_t$ exceed the threshold value used for movement detection, $\theta_T$. Changes in scale of the signal in different orientations, due to variation in the vertical component of rotations is also noticeable.

FIG. 11D illustrates a graph showing correlation coefficients between angular rates of FIG. 11C and cannula pressure against time for each of the static periods. The mean is 0.9148.

FIG. 11E illustrates a graph showing respiratory rates calculated from the angular rates of FIG. 11C and respiratory rates calculated from cannula pressure derived data against time for each of the static periods. The accelerometer-based rate is only defined for times surrounded by a full window of angular rate information, and therefore covers a further reduced set of time segments.

In several of the examples discussed above, the values of angles of rotation $\phi_t$ or the angular velocities $\omega_t$ have been used to provide respiration related signals, for example: to identify angular rotation and rotation rate of a patient's torso, to monitor breathing and respiratory rates. However, the values of the angles of rotation $\phi_t$ or the angular velocities $\omega_t$ can also be used to determine additional patient movement related parameters, such as patient speech as well as movement of the patient such as walking, running or climbing stairs.

The detection and identification of such additional movements can be used in determining periods of activity of the patient (when measurements of respiration would not be possible as the respiration movement component of the measurement signals would be masked or swamped by the additional movement) and static periods of rest of the patient (where respiration measurements would be feasible). Additionally, the detection and identification of such additional movements may provide context to the monitored values of $\phi_t$ and $\omega t$ by indicating, for example, when a patient was sleeping, walking, talking or running. Furthermore, an intensity of the level of additional movement could be gauged which would enable identification, for example, of periods of intensive exercise.

To further improve the accuracy of the respiration measurements, measurements captured during detected periods of activity or additional motion (i.e. motion over and above that of just respiratory related motion) could be disregarded and only utilized during a determined period of inactivity of the patient.

Figure 12:
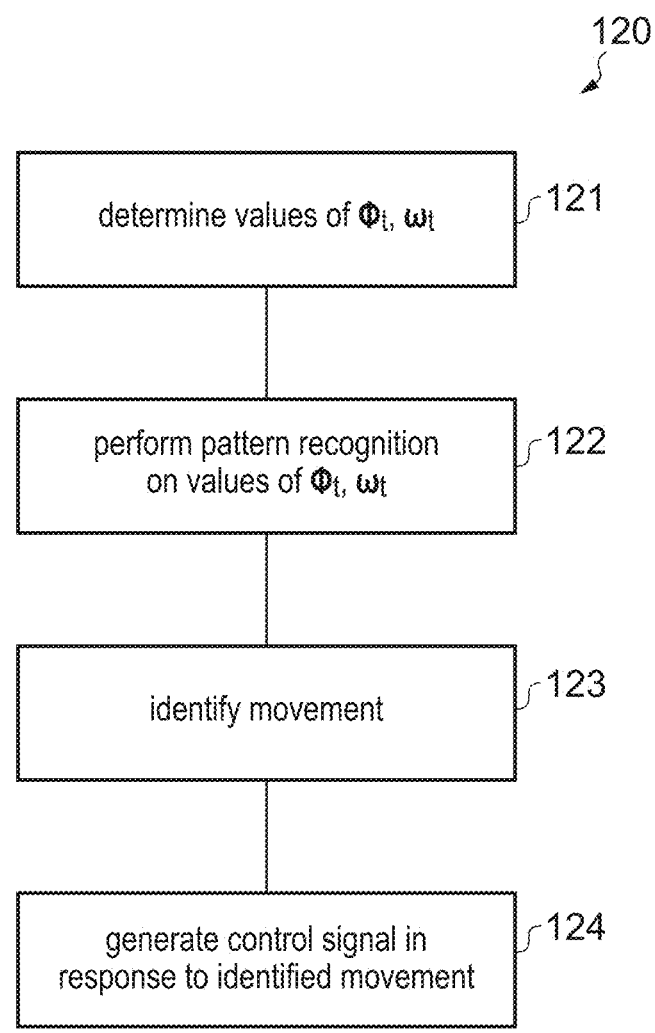
FIG. 12 schematically illustrates a flow diagram of another method for measuring oscillatory motion.

FIG. 12 schematically illustrates a flow diagram of another method 120 for measuring oscillatory motion.

In block 121 a series of values of angles of rotation $\phi_t$ or angular velocities $\omega_t$ are determined as previously discussed above.

In block 122, a pattern recognition algorithm is applied to the series of values of angles of rotation $\phi_t$ or the angular velocities $\omega_t$ to detect patterns, shapes and frequencies in the respective $\phi_t$, $\omega_t$ waveforms. Such patterns, shapes and frequencies of the wave form may be indicative of certain movements, such as respiratory related movements when the patient is static as discussed above, but also other non respiratory related movements such as a patient: speaking, walking or running.

In block 123, an identification of the movement is made based on the results of the pattern recognition. For example, the movement would be identified as any of, e.g.: breathing, speaking or patient movement such as walking, or running.

In block 124, a control signal is generated in response to the indentified movement. For example, if the movement were identified as just breathing, then control signal could cause the use of the measurements to determine respiration signals. If the movement were identified as some other movement (i.e. not related just to breathing) such as speaking, walking, or running then the control signal could be to disregard measurements for the use of determining respiration signals.

Although various embodiments of the present invention have been described above with reference to various examples, it should be appreciated that modifications to the examples given can be made without departing from the scope of the invention as claimed. Features described in the preceding description may be used in combinations other than the combinations explicitly described.

Although functions have been described with reference to certain features, those functions may be performable by other features whether described or not. Although features have been described with reference to certain embodiments, those features may also be present in other embodiments whether described or not.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method comprising:
receiving a plurality of signals from at least one sensor sensing oscillatory motion, the plurality of signals being related to a plurality of measurements of a direction of a vector parameter, wherein the at least one sensor is either directly or indirectly coupled to a body part that undergoes oscillatory motion during respiration;
determining a predominant measured direction of the vector parameter based on the plurality of measurements;
determining a plurality of angles of rotation between:
individual measured directions of the vector parameter of corresponding ones of the plurality of measurements, and
the predominant measured direction of the vector parameter;
determining a plurality of angular velocities based on the plurality of angles of rotation;
monitoring values of the angular velocities;
defining a first band of range of angular velocity values where an angular velocity value is greater than a first threshold value;
defining a second band of range of angular velocity values where an angular velocity value is less than a second threshold value;
defining a third band of range of angular velocity values where an angular velocity value is between the first and second threshold values;
registering a count of a cycle of oscillatory motion upon determining monitored values of angular velocity undergoing four band transitions; and
determining, based on the angular velocities with reference to (i) a predetermined relationship between angular velocity values and cannula pressure values, and (ii) a predetermined relationship between the cannula pressure values and flow rate values for nasal breathing, one or more of: a respiration pressure, a respiration flow rate, or an inspiratory flow.

2. The method as recited in claim 1, wherein the plurality of measurements comprise a plurality of pairs of sequential measurements of a direction of the vector parameter; the method further comprising:
determining an axis of rotation for each pair of sequential measurements, wherein the axis of rotation is defined as an axis about which the measured direction of the vector parameter rotates between a pair of sequential measurements of the direction of the vector parameter;
determining a predominant axis of rotation based on the determined axes of rotation; and
wherein an individual angle of rotation of the plurality of angles of rotation is further determined based on rotation about the predominant axis of rotation.

3. The method as recited in claim 1, further comprising determining, based on an individual angular velocity of the plurality of angular velocities, a change in volume of a user's chest.

4. An apparatus comprising:
a memory storing computer program instructions; and
a processor configured to execute the computer program instructions to cause the apparatus at least to perform the method of claim 1.

5. A non-transitory computer readable storage medium encoded with instructions that, when executed by a processor, performs the method of claim 1.

6. The method as recited in claim 1, further comprising determining a change between:
a measurement of the vector parameter, and
a sequential measurement of the vector parameter.

7. The method as recited in claim 6, further comprising determining if the change is greater than a threshold value; and
if the change is greater than a threshold value:
receiving a further plurality of signals related to a further plurality of measurements of a direction of the vector parameter;
re-determining the predominant measured direction of the vector parameter based on the further plurality of measurements; and
determining an angle of rotation between:
a measured direction of the vector parameter of one of the further plurality of measurements of the direction of the vector parameter, and
the re-determined predominant measured direction of the vector parameter.

8. The method as recited in claim 1, further comprising:
receiving a plurality of signals related to a plurality of measurements of a direction of a second vector parameter;
determining a predominant direction of the second vector parameter based on the plurality of measurements of the direction of the second vector parameter; and
determining an angle of rotation between:
a measured direction of the second vector parameter, and
the predominant direction of the second vector parameter.

9. The method as recited in claim 8, wherein the second vector parameter differs from the vector parameter.

10. The method as recited in claim 1, further comprising determining an angle of projection, wherein the angle of projection is defined as a projection of an individual angle of rotation of the plurality of angles of rotation onto a surface.

11. The method as recited in claim 10, wherein the surface comprises one of a plane or at least part of an ellipsoid.

12. The method as recited in claim 1, further comprising:
determining a series of values of angular velocities or angles of rotation; and
applying a pattern recognition algorithm to the series of values of angular velocities or angles of rotation.

13. The method as recited in claim 12, further comprising applying the pattern recognition algorithm to the series of values of angular velocities or angles of rotation in order to identify a motion.

14. The method as recited in claim 13, further comprising generating a control signal in response to identification of the motion.

15. An apparatus comprising:
an input interface configured to receive a plurality of signals from at least one sensor for sensing oscillatory motion, the plurality of signals being related to a plurality of measurements of a direction of a vector parameter, wherein in use the at least one sensor is either directly or directly coupled to a body part that undergoes oscillatory motion during respiration; and a controller configured to:

determine a predominant direction of the vector parameter based on the plurality of measurements;

determine a plurality of angles of rotation between:

individual measured directions of the vector parameter of corresponding ones of the plurality of measurements, and the predominant direction of the vector parameter;

determine a plurality of angular velocities based on the plurality of angles of rotation;

monitor values of the angular velocities;

define a first band of range of angular velocity values where an angular velocity value is greater than a first threshold value;

define a second band of range of angular velocity values where an angular velocity value is less than a second threshold value;

define a third band of range of angular velocity values where an angular velocity value is between the first and second threshold values;

register a count of a cycle of oscillatory motion upon determining monitored values of angular velocity undergoing four band transitions; and determine, based on the angular velocities with reference to (i) a predetermined relationship between angular velocity values and cannula pressure values, and (ii) a predetermined relationship between the cannula pressure values and flow rate values for nasal breathing, one or more of: a respiration pressure, a respiration flow rate, or an inspiratory flow.

16. A system comprising:

a sensor configured to measure a direction of a vector parameter;

a processor configured to generate a signal related to the direction of the vector parameter;

a transmitter configured to transmit the signal; and the apparatus according to claim 15.

17. The system as recited in claim 16, wherein the sensor configured to measure the direction of the vector parameter comprises at least one of:

a sensor configured to measure a gravitational field, a sensor configured to measure a magnetic field, or a sensor configured to measure an angular orientation.

* * * * *